(12) United States Patent
Adams et al.

(10) Patent No.: US 9,429,585 B2
(45) Date of Patent: *Aug. 30, 2016

(54) SAMPLING SYSTEM

(71) Applicant: EMD Millipore Corporation, Billerica, MA (US)

(72) Inventors: George Adams, Merrimack, NH (US); John Dana Hubbard, Billerica, MA (US); Aaron Burke, Hamilton, MA (US); Anthony DiLeo, Westford, MA (US)

(73) Assignee: EMD Millipore Corporation, Billerica, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/537,185

(22) Filed: Nov. 10, 2014

(65) Prior Publication Data

US 2015/0061865 A1 Mar. 5, 2015

Related U.S. Application Data

(62) Division of application No. 12/452,747, filed as application No. PCT/US2008/008834 on Jul. 18, 2008, now Pat. No. 8,957,778.

(60) Provisional application No. 60/963,016, filed on Aug. 2, 2007.

(51) Int. Cl.
*A61J 1/05* (2006.01)
*G01N 35/00* (2006.01)
(Continued)

(52) U.S. Cl.
CPC ......... *G01N 35/00732* (2013.01); *B01L 3/545* (2013.01); *C12M 33/00* (2013.01);
(Continued)

(58) Field of Classification Search
CPC .......... A61J 2205/60; A61J 1/10; A61J 1/12; A61J 1/14; A61B 2019/44; A61B 2019/448; G01N 1/10; G01N 1/20; G01N 1/2035; G01N 2001/1031
See application file for complete search history.

(56) References Cited

U.S. PATENT DOCUMENTS 3,728,694 A 4/1973 Rohrer
5,360,437 A 11/1994 Thompson
(Continued)

FOREIGN PATENT DOCUMENTS

CN 1201523 A 12/1998
CN 2605566 Y 3/2004
(Continued)

OTHER PUBLICATIONS

International Preliminary Report on Patentability received for PCT Patent Application No. PCT/US2008/008834, issued on Feb. 2, 2010, 7 pages.
(Continued)

*Primary Examiner* — Andrew Bee
(74) *Attorney, Agent, or Firm* — EMD Millipore Corporation

(57) ABSTRACT

The present invention uses a wireless memory/communication device at least on the one or more sample storage devices, preferably on both the one or more sample storage devices and the sampling holder, optionally the port on the equipment as well. Data such as that relating to the vessel, the location of the port on the vessel, the device, its manufacture date or lot number, the date of the installation, sterilization and/or taking of a sample along with the person who installed the device and/or took the sample can be read and preferably added to the wireless device when a read/write type of device as these events occur through a scanner/reader/writer device (fixed or hand held). The sample storage device in the laboratory can also then be read and recorded to track the sample storage device's life.

7 Claims, 5 Drawing Sheets

(51) Int. Cl.

| | | |
|---|---|---|
| *G01N 1/18* | (2006.01) | |
| *C12M 1/26* | (2006.01) | |
| *C12M 1/32* | (2006.01) | |
| *C12M 1/12* | (2006.01) | |
| *B01L 3/00* | (2006.01) | |
| *G01N 1/10* | (2006.01) | |
| *G01N 1/20* | (2006.01) | |

(52) U.S. Cl.
CPC ............ *C12M 33/06* (2013.01); *C12M 37/00* (2013.01); *G01N 1/18* (2013.01); *B01L 3/505* (2013.01); *B01L 2300/022* (2013.01); *G01N 2001/1031* (2013.01); *G01N 2001/205* (2013.01); *G01N 2035/00782* (2013.01); *G01N 2035/00801* (2013.01)

(56) References Cited

U.S. PATENT DOCUMENTS

| | | |
|---|---|---|
| 5,674,381 A | 10/1997 | Den Dekker |
| 5,866,907 A | 2/1999 | Drukier et al. |
| 5,892,706 A | 4/1999 | Shimizu et al. |
| 5,923,001 A | 7/1999 | Morris et al. |
| 6,032,543 A | 3/2000 | Arthun et al. |
| 6,140,139 A | 10/2000 | Lienau et al. |
| 6,285,285 B1 | 9/2001 | Mongrenier |
| 6,366,206 B1 | 4/2002 | Ishikawa et al. |
| 6,617,963 B1 | 9/2003 | Watters et al. |
| 6,717,154 B2 | 4/2004 | Black et al. |
| 6,779,575 B1 | 8/2004 | Arthun |
| 6,795,339 B2 | 9/2004 | Ooishi |
| 7,048,775 B2 | 5/2006 | Jornitz et al. |
| 8,028,835 B2 | 10/2011 | Yasuda et al. |
| 8,111,159 B2 | 2/2012 | Andreasson et al. |
| 8,405,508 B2 | 3/2013 | Burke |
| 8,497,775 B2 | 7/2013 | Burke |
| 2001/0007532 A1 | 7/2001 | Sato et al. |
| 2003/0072676 A1 | 4/2003 | Fletcher-Haynes et al. |
| 2003/0156449 A1 | 8/2003 | Ooishi |
| 2003/0164401 A1 | 9/2003 | Andreasson et al. |
| 2003/0183699 A1 | 10/2003 | Masui |
| 2004/0173456 A1 | 9/2004 | Boos et al. |
| 2005/0040433 A1 | 2/2005 | Nozieres et al. |
| 2005/0132821 A1 | 6/2005 | Furey et al. |
| 2005/0205658 A1 | 9/2005 | Baker et al. |
| 2005/0210302 A1 | 9/2005 | Kato et al. |
| 2006/0016897 A1 | 1/2006 | Yasuda et al. |
| 2006/0092013 A1 | 5/2006 | Hager et al. |
| 2006/0201263 A1 | 9/2006 | Furey et al. |
| 2006/0211995 A1 | 9/2006 | Myhrberg et al. |
| 2006/0220868 A1 | 10/2006 | Takasawa et al. |
| 2006/0272432 A1 | 12/2006 | Belongia |
| 2007/0080783 A1 | 4/2007 | Ghosh et al. |
| 2007/0217717 A1 | 9/2007 | Murray |
| 2008/0042837 A1 | 2/2008 | Burke |
| 2008/0137399 A1 | 6/2008 | Chan et al. |
| 2010/0006204 A1 | 1/2010 | Burke et al. |
| 2012/0061463 A1 | 3/2012 | Burke |
| 2014/0252084 A1 | 9/2014 | Burke et al. |

FOREIGN PATENT DOCUMENTS

| | | |
|---|---|---|
| CN | 1658233 A | 8/2005 |
| CN | 1695161 A | 11/2005 |
| CN | 1877288 A | 12/2006 |
| DE | 29819987 U1 | 1/1999 |
| EP | 1001265 A2 | 5/2000 |
| EP | 1754973 A2 | 2/2007 |
| GB | 1325961 A | 8/1973 |
| GB | 1527341 A | 10/1978 |
| JP | 11-297963 A | 10/1999 |
| JP | 11-514741 A | 12/1999 |
| JP | 2003-243631 A | 8/2003 |
| JP | 2005-17177 A | 1/2005 |
| JP | 2005-503669 A | 2/2005 |
| JP | 2005-503870 A | 2/2005 |
| JP | 2005-181336 A | 7/2005 |
| JP | 2006-30035 A | 2/2006 |
| JP | 2006-39773 A | 2/2006 |
| JP | 2006-90937 A | 4/2006 |
| JP | 2006-276033 A | 10/2006 |
| WO | 96/14043 A1 | 5/1996 |
| WO | 97/16715 A1 | 5/1997 |
| WO | 01/08106 A2 | 2/2001 |
| WO | 01/47466 A1 | 7/2001 |
| WO | 03/026724 A1 | 4/2003 |
| WO | 2004/023389 A2 | 3/2004 |
| WO | 2004/028631 A1 | 4/2004 |
| WO | 2006/032326 A1 | 3/2006 |
| WO | 2006/041965 A2 | 4/2006 |

OTHER PUBLICATIONS

International Search Report and Written Opinion received for PCT patent Application No. PCT/US2008/008834, mailed on Feb. 18, 2009, 8 pages.

Extended European Search Report received for EP Patent Application No. 07253109.8, mailed on Oct. 9, 2007, 6 pages.

Extended European Search Report received for EP patent Application No. 08164914.7, mailed on Mar. 12, 2010, 6 pages.

"AN200—Advantages of the FM24C16", Ramtron International Corporation, Jan. 1999, pp. 1-2.

"GammaTag; Gamma Sterilization RFID Tags" AdvantaPure, Tech Sheet 40, rev. b, Mar. 17, 2008, 4 pages.

"New RFID Tag Withstands Industrial Sterilization", RFID Journal, Dec. 13, 2006, 2 pages.

"Ramtron Vendor Test Reports", Dec. 2, 1996, 15 pages.

"A Scientific Study of the Problems of Digital Engineering for Space Flight Systems, With a View to Their Practical Solution", Ramtron Serial FRAM Heavy Ion Test, BNL, Nov. 1998, 1 page.

Chu et al., "The Endurance Performance of 05 μm FRAM Products", Technical paper, Ramtron International Corporation, May 2005, pp. 1-3.

Kamp et al., "Adaptable Ferroelectric Memories for Space Applications", Non-Volatile Memory Technology Symposium, Nov. 15-17, 2004, pp. 149-152.

Namkung et al., "Reliability and Endurance of FRAM; a case study", Non-volatile Memory Technology Symposium, Nov. 4, 2002, 5 pages.

Nguyen et al., "Radiation Response of Emerging FeRAM Technology", Nonvolatile Memory Workshop, Nov. 7, 2001, pp. 1-3.

Philpy et al., "Reliability of Ferroelectric Memory for High-Rel and Space Applications", Celis Semiconductor Corporation, Presented at the Jet Propulsion Laboratory MRQ conference, Oct. 1999, pp. 1-5.

Takasu, Hidemi, "Ferroelectric Memories and Their Applications", Microelectronic Engineering, vol. 59, No. 1-4, Nov. 2001, pp. 237-246.

"Total Dose Radiation Tests at FRAM Non-Volatile Memories", vH&S Internal Memo, Nov. 30, 1996, pp. 1-5.

"Escort Memory Systems", Interphex Trade Show, NewAge-Advantapure Discussions, Mar. 21, 2006 and May 10, 2006, 1 page.

"Fujitsu Develops High Capacity, High Speed Chip with Embedded FRAM for RFID Tags", Fujitsu Limited,, Feb. 27, 2003, 3 pages.

"Fujitsu Introduces New, Light, Cost-Effective RFID Tags with 256 Bytes of FRAM for Product Tracking, Distribution Applications", Fujitsu Microelectronics America, Inc., Aug. 9, 2005, 2 pages.

"New Age Industries Purchase Order", Order of 2500 gamma radiation resistant RFID tags from EMS, Jul. 25, 2006, 1 page.

"RF SAW, Inc. Announces Gamma Radiation Hard RFID Tags: Doses Up to 5 Mega Rads—500 Million Ergs/Gm—with No Measurable Degradation", Business Wire, Dec. 10, 2003, 1 page.

"RFID Accredited Workshop Added to INTERPHEX2006 Pre-Conference Program Recent FDA Symposium Exposes Importance of RFID Education", INTERPHEX2006, Feb. 28, 2006, 3 pages.

"RFID tag with 256 bytes of FRAM", EE Times India, Aug. 12, 2005, 1 page.

(56) References Cited

OTHER PUBLICATIONS

Benedetto et al., "Radiation Evaluation of Commercial Ferroelectric Nonvolatile Memories", IEEE Transactions on Nuclear Science, vol. 38, No. 6, Dec. 1991, pp. 1410-1414.
Coic et al., "A Study of Radiation Vulnerability of Ferroelectric Material and Devices", IEEE Transactions on Nuclear Science, vol. 41, No. 3, Jun. 1994, pp. 495-502.
Derbenwick et al., "Advances in FeRAM Technologies", Celis Semiconductor Corporation, 2000, 3 pages.
Derbenwick et al., "Advances in FeRAM Technology", Non Volatile Memory Technology Symposium, Nov. 15-16, 2000, 23 pages.
Derbenwick et al., "Ferroelectric Memory : On the Brink of Breaking Through", IEEE, Circuit & Devices, Jan. 2001, pp. 20-30.
Gee, Tim "Could SAW RFID Tags Serve Health Care?", Patent Safety, available online at <http://medicalconnectivity.com/2006/04/26/#a685>, Apr. 26, 2006, 1 page.
Krause, Reinhardt "Motorola Signs Ferroelectric RAM Deal", Electronic News, Jun. 6, 1994, 2 pages.
Scott et al., "Radiation Effects on Ferroelectric Thin-Film Memories: Retention Failure Mechanisms", Journal of Applied Physics, vol. 66, No. 3, Aug. 1, 1989, pp. 1444-1453.

SAMPLING SYSTEM

CROSS-REFERENCE TO RELATED APPLICATIONS

This application is a divisional application of U.S. application Ser. No. 12/452,747, filed May 3, 2010 which is the U.S. National Stage Application of International Application No.: PCT/US2008/008834, filed on Jul. 18, 2008, which claims priority to U.S. Application No. 60/963,016 filed Aug. 2, 2007.

The present invention relates to a sampling system. More particularly, it relates to a sampling system having a port and one or more sample containers that are wirelessly enabled to track location and/or other information.

BACKGROUND

Traditional sample systems for pharmaceutical or biopharmaceutical processes use large stainless steel systems that include steam traps and the like to at least aseptically clean the system between uses.

U.S. Pat. No. 6,032,543 introduced to disposable sterile sampling system comprised of a carousel or holder into which one or more septum containing sampling collection devices are attached. This is sold as the NovaSeptum® sampling device available from Millipore Corporation of Billerica, Mass. The devices have a sample taking device, in this instance a septum surrounding a needle at the front end with the rear portion of the needle being attached to a flexible conduit such as a tube or hose which in turn is attached to a sample storage device such as a bag as shown in the patent or as a syringe as described in US 2006/0211995 A1 and sold as the NovaSeptum® AV system by Millipore Corporation of Billerica, Mass. The internal area between the septum and sample storage device, in the first instance a bag and in the syringe its inner volume, is isolated from the environment and sterilized (gamma or beta radiation, ETO, etc) before assembly into a holder. The holder is liquid tightly attached to a port of a bioreactor or other piece of equipment such as a storage vessel, mixing vessel and the like, the septum based sample taking devices are loaded into the holder and then the face of the system (holder and septum of the sample taking device is sterilized along with the rest of the interior of the equipment. The vessel is then filled and samples are taken as needed during processing. Information concerning the sample, when and where it was taken and by whom is recorded by hand either onto a paper label that is then attached to the sample storage device or in a notebook.

US 2005/0132821 A1 and US 2006/0201263A1 add to this concept by eliminating the need for a septum and yet provide a sterile connection and sample collection system. The use of shafts mounted in a holder with tubes connected to the rear portions of the shafts which in turn are connected to s sample storage device such as bags. The shafts are mounted in the holder or body and isolated from the environment and then sterilized by radiation such as gamma or beta, steam, ETO or the like.

US 2006/0272432A1 is also a septum-less system that uses slidable gates to selectively open or close a pathway from the vessel to a conduit and then to a sample storage device.

All of these systems are then mounted to a port and the face of the port is sterilized with the interior of the vessel to provide a sterile pathway for the samples. The shafts are moved either linearly or rotationally into alignment to draw a sample or the gates are moved linearly to open a passage for the liquid sample. As with the NovaSeptum design discussed above, the information is recorded separately and then attached to the sample holder or placed in a notebook.

What is needed is a better method and device for tracking such information in a foolproof manner.

SUMMARY

The present invention uses a wireless memory/communication device at least on the one or more sample storage device such as bags, bottles or syringes, preferably on both the one or More sample storage device and the sampling holder, optionally the port on the equipment as well.

The use of RFID, Zigbee®, Bluetooth® and other wireless systems is acceptable.

In one embodiment, a read only tag, such as a read only RFID tag is used on the one or more sample storage devices. The tag(s) contain an identity code for the sample storage device. This is then used with a scanner (hand held or fixed) to track the usage of this sample storage device such as the date of installation and on which sampling holder, the date a sample taking and the like.

Preferably, the sample storage device utilizes a read/write memory device, such as a RFID, Zigbee®, Bluetooth® and other wireless read/write tag. Data such as that relating to the vessel, the location of the port on the vessel, the date of the installation, sterilization and/or taking of a sample along with the person who installed the device and/or took the sample can be added to the tag on the sample storage device as these events occur through a scanner/reader/writer device (fixed or hand held). The sample storage device in the laboratory can also then be read and recorded to track the sample storage device's life.

More preferably, the system itself, such as the holder also has a memory/communication device and it can transfer its information to the device on the sample storage device, either directly or through an intermediate reader/writer.

IN THE FIGURES

DETAILED DESCRIPTION

Figure 1:
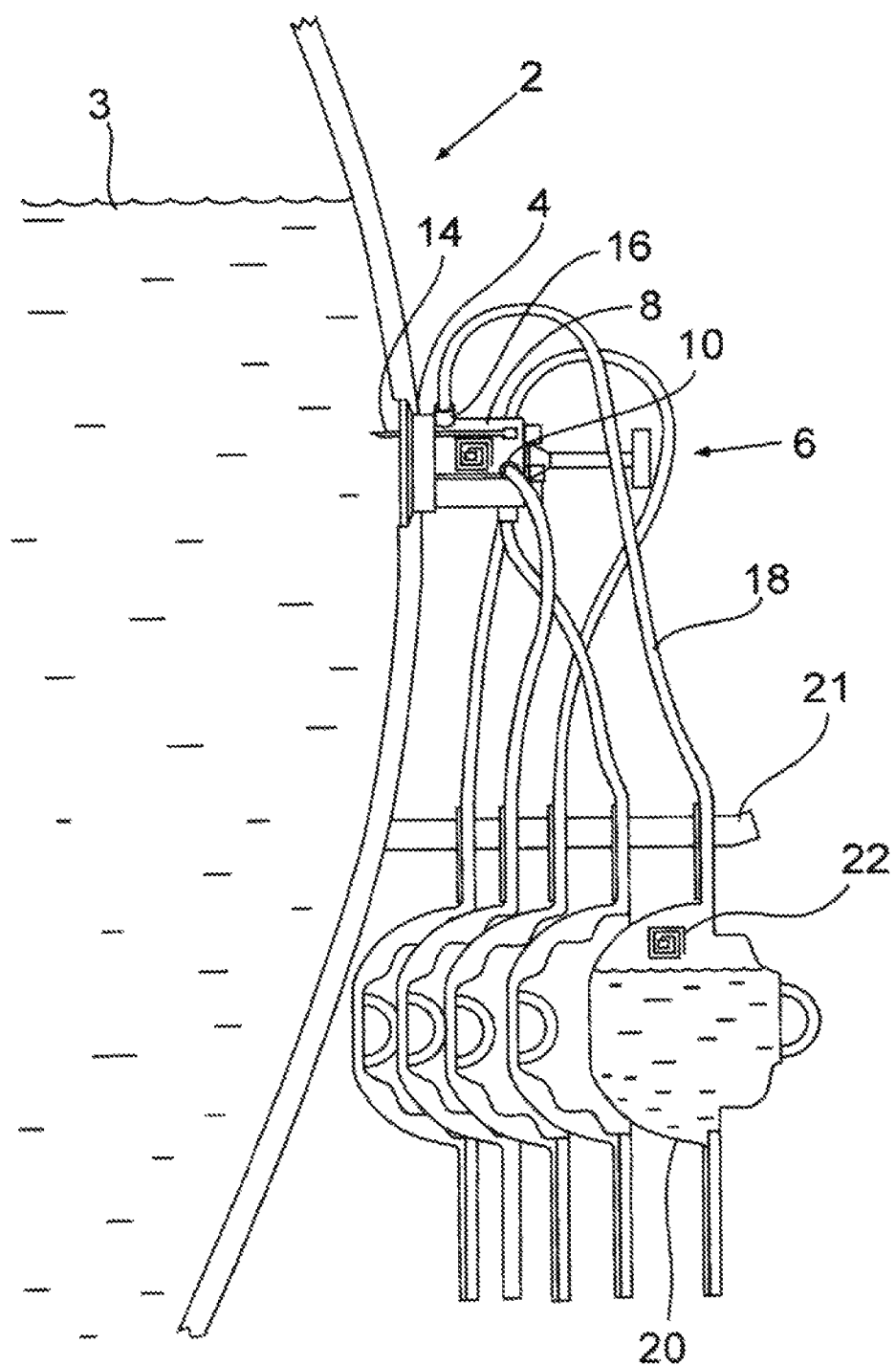
FIG. 1 shows a first embodiment of the present invention in cross-sectional view.

FIG. 1 shows a first embodiment of the present invention. A vessel 2, such as a bioreactor, storage vessel, mixing, tank and the like, contains one or more ports 4 (one shown) such as an Ingold® port or a NovaSeptic® port onto or into which a sampling system 6 is mounted. The vessel 2 contains a liquid 3 that needs to be sampled from time to time. In this example, a NovaSeptum® sampling system, according to U.S. Pat. No. 6,032,543 is shown. The system 6 has a holder 8 mounted to the port 4 of the vessel 2. One or more sample sterile collectors 10 are loaded in the holder 8.

The collectors 10 have a septum (not shown) containing a sample gatherer 14 that is open to the remainder of the collector 10 when inserted into the vessel 2. In this instance it is a needle that passes through a septum (not shown) to enter the vessel 2 and collect a sample from the liquid 3. The rear portion 10 of the gatherer 14 is connected to a collection tube 18 which in turn is connected to one or more sample storage devices 20, in this embodiment shown as bags although it may be bottles, syringes or other vessels used to collect and store samples.

The sample storage device(s) 20 each contain a wireless memory/communications device 22 such as a RFID tag, a Zigbee® device, a Bluetooth® device and the like. The wireless device may be mounted to the sample storage device as a plastic encasing disk which covers the wireless device and prevents it from being damaged. Alternatively, it may be laminated onto the sample storage device directly or to a label which is applied to the sample storage device. Such printed labels/wireless devices are known and available from a number of sources including PrintTech and Zebra Technologies. Alternatively, the device may be formed into a plastic tag which has a strap that can be attached to the sample storage device or the tube connected to the sample storage device. In another embodiment, it can be laminated into the film of the sample storage device itself.

Figure 4:
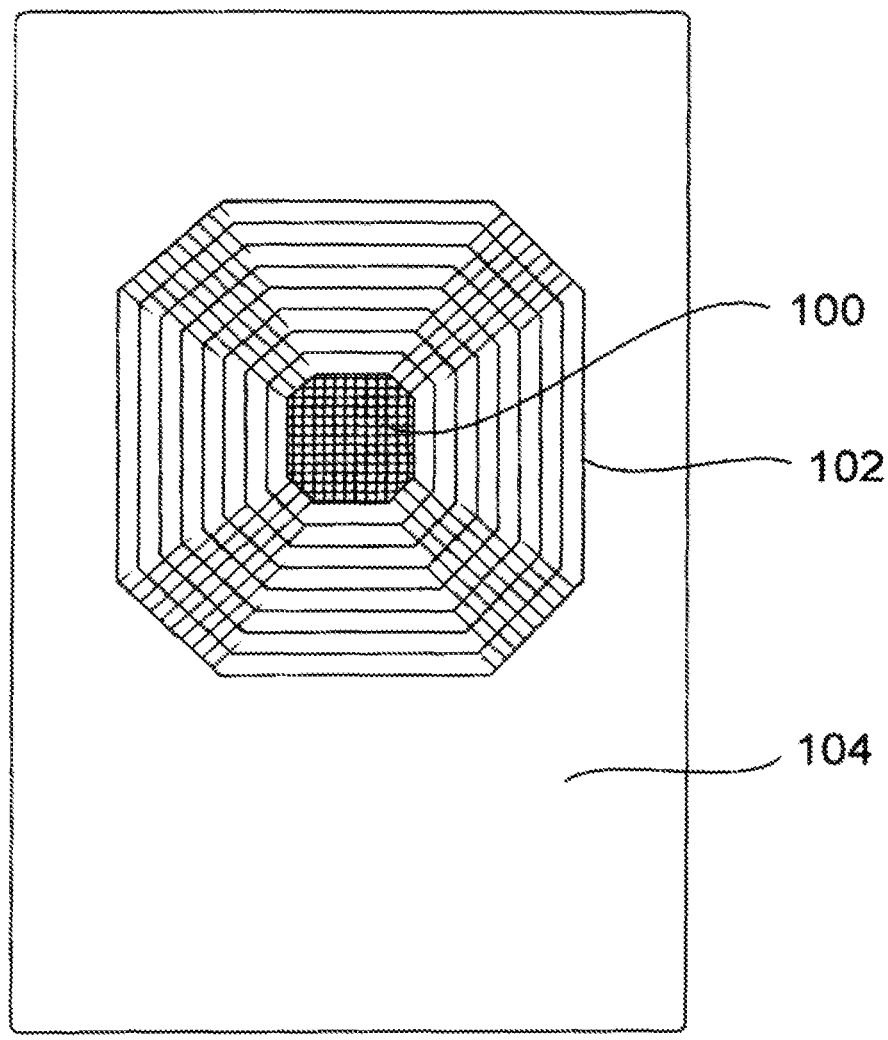
FIG. 4 shows a wireless device useful in the invention in top down planar view.

The wireless device essentially comprises two components as shown in FIG. 4, a microchip 100 and an antenna 102. This is generally attached to a plastic surface or sheet 104 or encapsulated with an epoxy (not shown). The device can be of any frequency although high frequency (HF) and ultrahigh frequency (UHF) are the most popular. Additional elements may be added if desired such as a battery or capacitor to provide the device with its own power source, if desired. Most systems however are passive and rely on the signal from the reader/writer to power up the device as needed.

In this embodiment, the device 22 is a read only device containing at least a unique identifier for that sample storage device, such as an alphanumeric serial number.

In use, before, during or after the sample storage device(s) 20 have been loaded into the holder 8, they are read by a scanner (not shown) which may be a fixed station such as a desktop reader like the AccuSmart™ reader available from Millipore Corporation of Billerica, Mass. or a hand held device such as the Hose Tracker™ reader available from Advantapure of South Hamilton, Pa.

This information as to the identity of the sample storage device and optionally, at least one trackable-event such as its location, date of installation, installer, etc, can be entered into the scanner. It may be stored there or it may be downloaded to a computer or network connection or the internet if desired.

Upon or just after sampling, the device 22 can again be scanned by the reader to record the use date, time, location, etc.

When the sample storage device 20 reaches the testing laboratory, the device 22 can be scanned to record its arrival and/or analysis. Optionally, the name of the tester, the test to be performed, the storage, length of time before testing and the like may also be added to the scanner or other storage item a computer or network connection or the internet by the laboratory to track its workload and generate its reports.

In the Figures that follow, the same reference numbers are used to if they represent the same elements discussed above in regard to FIG. 1.

Figure 2:
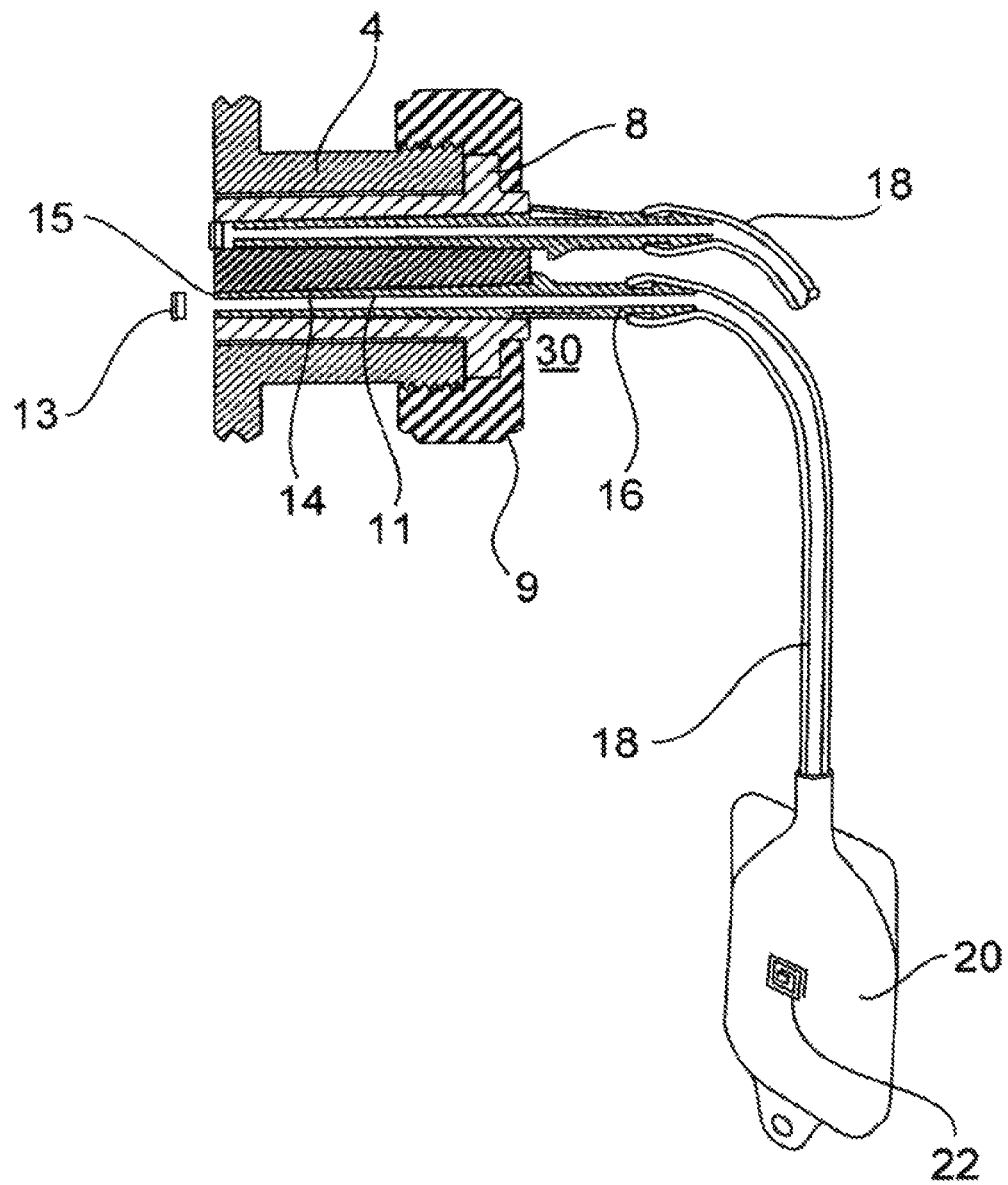
FIG. 2 shows a second embodiment of the present invention in cross-sectional view.

In another embodiment as shown in FIG. 2, the wireless device 22, this time used on a sampling system according to US 2005/0132821A1, although a NovaSeptum® system or any other sampling device can also be used, is a read/write device so that data relating to one or more trackable events such as identity, location, installation, use and testing dates and times, etc. can be recorded on to the device 22 itself. Optionally, the data may also be downloaded to a computer, network or internet site as described above in the earlier embodiment. In this embodiment, the holder 8 may be retained to the port by a means such as a nut 9 as shown or by other means such as a clamp. The gatherer 14 in this case is not a needle but rather a shaft having a central bore 11 and the end adjacent the inner volume of the vessel 2 covered by a cap 13. A passageway 15 is behind the cap 13 provides a fluid pathway between the inner volume of the vessel 2 and the central bore of the gatherer 14 when the shaft is extended into the volume to take a sample from the liquid 3. The sample then flows into the tube 18 and sample storage device 20.

An alternative sample device according to US 2005/0112821A1 (not shown), which rotates a shall and the holder relative each other and/or the port to selectively expose and provide access of a shaft to the inner volume of the vessel 2 may be used as well if desired and it functions in a similar manner.

In use, the wireless device 22 arrives at to user's facility with manufacturer and sterilization data, etc. already loaded on to it or contained on a secure website of the manufacturer which can be accessed by providing the website with the identification number contained on the wireless device. When mounted to a vessel 2, various data such as location, date of installation, installer etc, is recorded on the device 22. If desired, the date/time of sterilization of the system 6 in place on the vessel 2 can also be recorded.

When a sample is taken, the day/time/user and other relevant trackable data can be recorded onto the device 22 which is then sterilely disconnected from the system such as by the crimp/crimper cutter device of U.S. Pat. No. 6,779,575 and taken to a laboratory for testing or stored as a retain.

If desired, the date/time of receipt at the lab or the storage facility can be recorded when it is received. Additionally, the data of the device 23 and/or computer, network or internet can also be downloaded and/or updated. Likewise, information regarding the tests conducted, the tester's identification and the like can also be added to the tag.

For storage applications, the device 22 or the computer network or internet site may contain specific storage instructions such as temperature to be maintained at, length for storage and the like.

Figure 3:
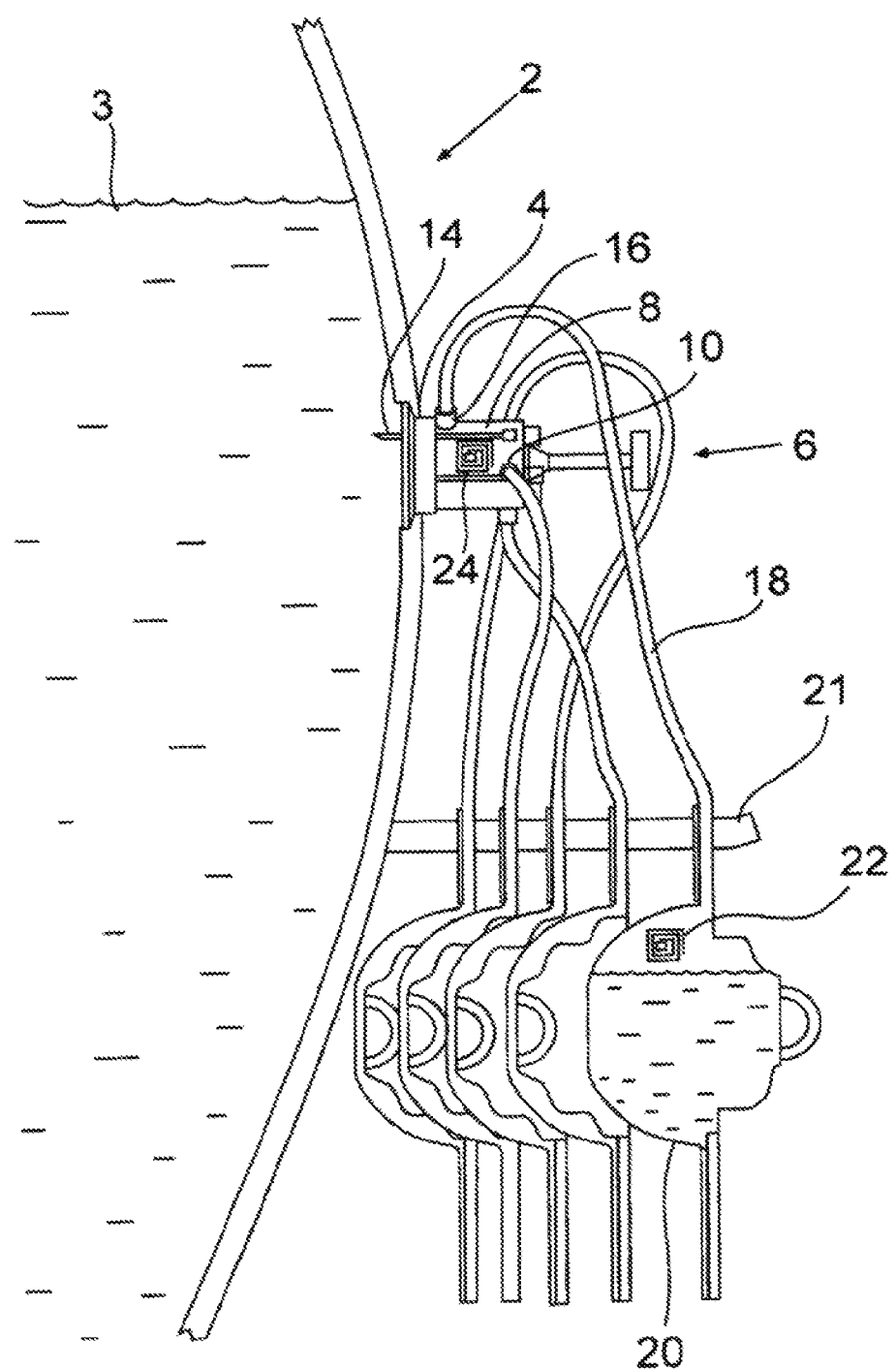
FIG. 3 shows a third embodiment of the present invention in cross-sectional view.

In a third embodiment as shown in FIG. 3, the system 6, such as the holder 8 which holds the sample collectors 10 contains its own wireless memory/communication device 24.

In this way, information relating to the system 6 such as manufacturing information, installation data, sterilization data, loading data (of collectors 10), location on the vessel 2 and/or in the facility can be loaded onto the second wireless device 24.

One can then scan the second device 24 when adding or using a sampling collector 10 so as to provide the first wireless device 22 of the collector 10 with some or all of the data of the system 6. This may be done directly from the second device 24 to the first device 22 or through an intermediary scanner such as a hand held scanning device (not shown).

Figure 5:
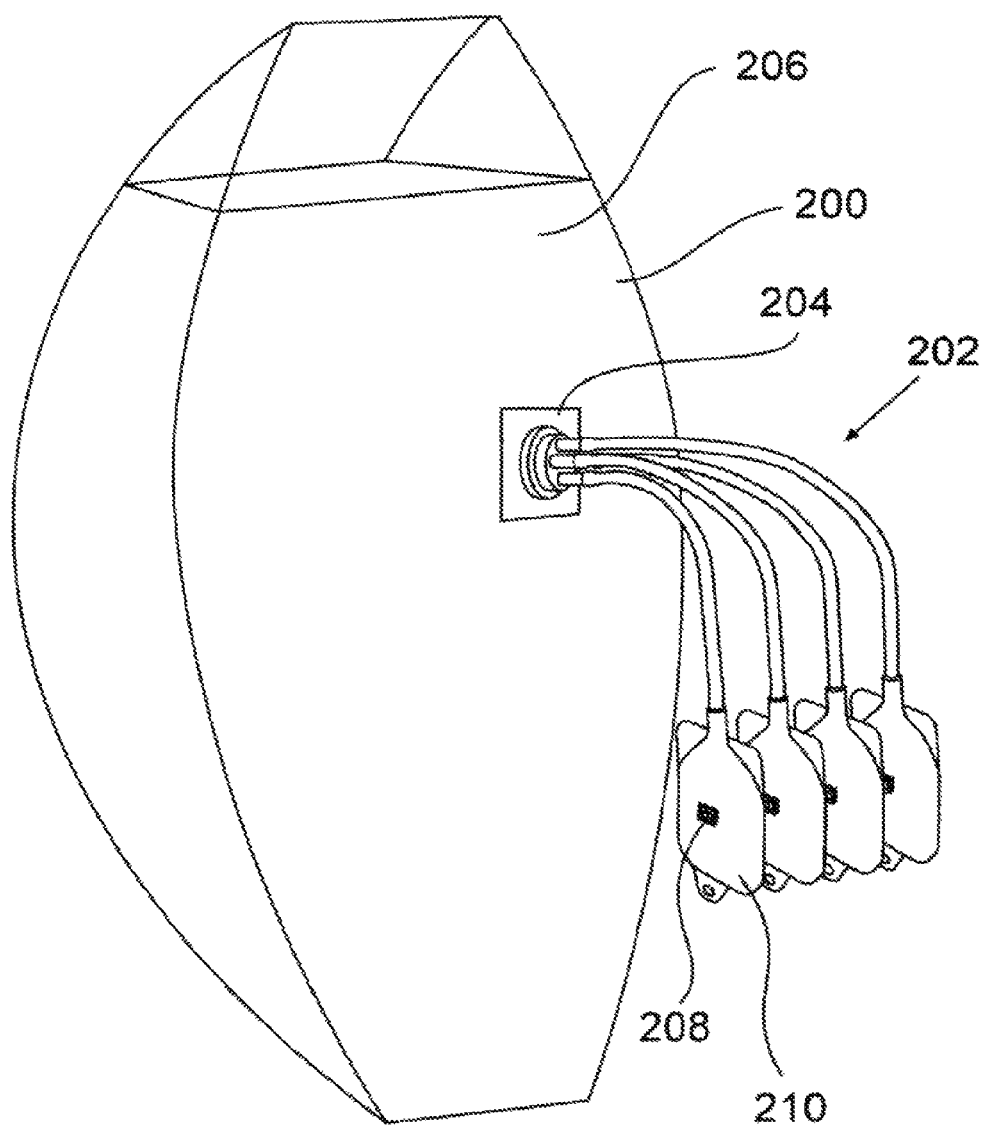
FIG. 5 shows another embodiment of the present invention in planar view.

FIG. 5 shows a sampling device according to the present invention used on a disposable vessel such as a plastic bag or rigid plastic container 200. A sampling system 202 is similar to those discussed above in relation FIG. 1-3 and is attached to the disposable vessel 200 such as by a port 204 which has been attached to an opening (not shown) in the vessel 200. This can be by heat sealing or welding (solvent or sonic energy) the port to or around the opening. Alternatively one can use a threaded fitting that extends through the opening from the interior of the vessel and a nut on the outside that match with the threads to forma liquid tight fitting. Likewise one can use a plastic titling inside the vessel 200 with a open neck that extends through the opening to the exterior of the vessel 200 and a second piece of plastic that can be sealed to the exterior surface of the neck to hold the fitting in place in the opening in a liquid tight manner. A wireless device 208, at least a read device, and preferably a read/write device as described above is used on at least each of the sample storage device 210. Optionally a second device (not shown) may be attached to the vessel or the port 204 if desired. The vessel 200 and sampling system 202 are made and sealed from the outside environment and then sterilized such as by radiation (gamma or beta), ethylene oxide or the like. If gamma radiation is used, a gamma stable wireless device such as is taught by U.S. application Ser. No. 11/501,446, filed Aug. 9, 2006, the teachings of which are incorporated herein by reference.

A sample of the liquid 206 is taken in a manner identical to that described in FIG. 1-3 above.

A process for using the invention comprises providing a collection system such as a NovaSeptum® device having a holder and one or more collection devices mounted therein. Each collection device is formed of a gatherer 14 of some type, such as a septum covered needle, or rigid tube or hollow shaft and the like, a conduit 18 such as a plastic tube attached to a rearward portion of the gatherer 14 and a sample storage device 20 such as a bag, syringe or bottle attached to the rearward portion of the conduit. The collection devices are rendered sterile in their interior before mounting onto the vessel. At least the one or more collection devices 20 contain a wireless communications and information storage device 22 as described herein above. Optionally, the holder 8 also contains a second wireless communications and information storage device 24 as described herein above. The system is mounted to a vessel 2 through a port 4 or opening in a liquid tight manner. The portion of the system that has been exposed to the environment, generally just the face of the holder 8 and the collectors 10 mounted in it is then sterilized in place. Information and if desired, at least one trackable event, on the first wireless device 22, and if present, the second wireless device 24, is taken. This information can be, but is not limited to, identity, location, date of installation, sampling, installer, installation date, etc. The vessel 2 is filled and a sample is taken and information and if desired at least one other trackable event is taken on the first wireless device 22, and if present the second wireless device 24. This information and for trackable event(s) can be stored on the first and/or second wireless device 22/24 and optionally the scanner (not shown) which may be a fixed station such as a desktop reader like the AccoSmart™ reader available from Millipore Corporation of Billerica, Mass. or a band held device such as the Hose Tracker™ available from Advantapure of South Hamilton, Pa. Alternatively or additionally, the information may be uploaded to a computer, a control system, a network or an internet address.

A system according to any of the embodiments allows one to electronically collect and/or store one or more trackable events such as data relating to the sampling system, its installation, use and if done, testing results.

By using the sterile disposable sampling systems, one is able to form a liquid tight, hermetic seal between the system and the interior of the vessel so that sterile samples can be taken.

The wireless device enabled system of the present invention eliminates any error as to location, date, time, user and the like and allows one to use good manufacturing practices (GMP) and good laboratory practices (GLP) in sampling systems.

What is claimed:

1. A process of tracking samples comprising the steps of providing a vessel having an interior for containing a liquid to be sampled, attaching a sample collecting device in a liquid tight hermetically sealed manner, the device having a sample collection holder, the sample collection holder having a second wireless memory/communication device directly attached to the sample collection holder, wherein more than one sample collector can be attached to the sample collection holder, each sample collector having a selectively closed front and a fluid open pathway to a rear portion of each sample collector, a conduit connected to a rear portion of the device, at least one sample storage device connected to a downstream portion of the conduit and a first wireless memory/communication device attached to the at least one sample storage device, wherein information from the second wireless memory/communication device is written to the first wireless memory/communication device when each sample storage device is attached to the sample collection holder, sterilizing the interior of the vessel and the sample collecting device, filling the vessel with a liquid to be sampled, conducting a first scanning of the first wireless device to determine one or more attributes of the at least one sample storage device, reading the one or more attributes and loading one or more trackable events onto the first wireless device during the first scanning and wherein the first wireless device is a read/write device.

2. The process of claim 1 further comprising the second wireless device is a read/write device.

3. The process of claim 1 wherein the at least one sample storage device is selected from the group consisting of bags, syringes and bottles.

4. The process of claim 1 wherein the one or more attributes of the first scanning are selected from the group consisting of the identity of the at least one sample storage device, the location of the at least one sample storage device, the date of installation of the at least one sample storage device, the installer of the at least one sample storage device, the date of sterilization of the vessel interior, the method of sterilization of the vessel interior and the liquid within the vessel.

5. The process of claim 1 further comprising operating the more than one sample collectors to obtain a sample of the liquid from the vessel and conducting a second scanning of the first wireless device on the at least one sample storage device containing the sample from the vessel to load one or more trackable events onto the first wireless device of the at least one sample storage device during the second scanning and wherein the one or more trackable events of the second scanning is one or more attributes selected from the group consisting of the date of the sample, the time of taking the sample and the person taking the sample.

6. The process of claim 1 further comprising moving the at least one sample storage device to a testing laboratory and conducting a third scanning of the first wireless device to load one or more trackable events onto the first wireless device of the at least one sample storage device during the third scanning and wherein the one or more trackable events of the third scanning is one or more attributes selected from the group consisting of the date of the arrival of the sample, the date of analysis of the sample, the name of the tester, the name of the test to be performed, the storage condition of the sample before testing, the length of time before testing and the results of the testing.

7. A process of tracking samples comprising the steps of providing a vessel having an interior for containing a liquid to be sampled, attaching a sample collecting device in a liquid tight hermetically sealed manner, the device having a sample collection holder having a second wireless memory/communication device directly attached to the sample collection holder, and one or more sample collectors, each of the one or more sample collectors having a selectively closed front and a fluid open pathway to a rear portion of the sample collector, a conduit connected to a rear portion of the device, at least one sample storage device connected to a downstream portion of the conduit and a first wireless memory/communication device attached to the at least one sample storage device, wherein information from the second wireless memory/communication device is written to the first wireless memory/communication device when the at least one sample storage device is attached to the sample collection holder, sterilizing the interior of the vessel and the sample collecting device, filling the vessel with a liquid to be sampled, conducting a first scanning of the first wireless device to determine one or more attributes of the at least one sample storage device, reading the one or more attributes and loading one or more trackable events onto the first wireless device during the first scanning and wherein the first wireless device is a read/write device wherein the one or more attributes of the first scanning are selected from the group consisting of the identity of the at least one sample storage device, the location of the sample storage device, the date of installation of the at least one sample storage device, the installer of the at least one sample storage device, the date of sterilization of the vessel interior, the method of sterilization of the vessel interior and the liquid within the vessel, operating the one or more collectors to obtain a sample of the liquid from the vessel into at least one sample storage device and conducting a second scanning of the first wireless device on the at least one sample storage device containing the sample from the vessel to load one or more trackable events onto the first wireless device of the at least one sample storage device during the second scanning and wherein the one or more trackable events of the second scanning is one or more attributes selected from the group consisting of the date of the sample, the time of taking the sample and the person taking the sample, and moving the at least one sample storage device to a testing laboratory and conducting a third scanning of the first wireless device to load one or more trackable events onto the first wireless device of the at least one sample storage device during the third scanning and wherein the one or more trackable events of the third scanning is one or more attributes selected from the group consisting of the date of the arrival of the sample, the date of analysis of the sample, the name of the tester, the name of the test to be performed, the storage condition of the sample before testing, the length of time before testing and the results of the testing.

* * * * *